United States Patent
Arnholt et al.

(10) Patent No.: US 10,285,672 B2
(45) Date of Patent: May 14, 2019

(54) ADJUSTABLE THROW PERCUTANEOUS NEEDLE

(71) Applicant: Boston Scientific Scimed, Inc., Maple Grove, MN (US)

(72) Inventors: Devon N. Arnholt, Shoreview, MN (US); Jonathan P. Fettig, Forest Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 482 days.

(21) Appl. No.: 15/053,756

(22) Filed: Feb. 25, 2016

(65) Prior Publication Data

US 2016/0249893 A1  Sep. 1, 2016

Related U.S. Application Data

(60) Provisional application No. 62/121,099, filed on Feb. 26, 2015.

(51) Int. Cl.
*A61B 10/02* (2006.01)

(52) U.S. Cl.
CPC ...... *A61B 10/0266* (2013.01); *A61B 10/0275* (2013.01); *A61B 2010/0208* (2013.01)

(58) Field of Classification Search
CPC ............ A61B 10/0266; A61B 10/0275; A61B 2010/0208
See application file for complete search history.

(56) References Cited

U.S. PATENT DOCUMENTS

| 2,516,492 | A | 7/1950 | Turkel |
| 5,156,160 | A | 10/1992 | Bennett |
| 2005/0075580 | A1* | 4/2005 | Leigh ................. A61B 10/0266 600/567 |
| 2009/0299220 | A1 | 12/2009 | Field et al. |
| 2010/0312141 | A1 | 12/2010 | Keast et al. |
| 2012/0253230 | A1 | 10/2012 | Williams et al. |
| 2015/0209100 | A1 | 7/2015 | Ineson |
| 2015/0359560 | A1* | 12/2015 | Bakhtyari-Nejad-Esfahani .......... A61B 10/0275 600/424 |

* cited by examiner

*Primary Examiner* — Sean P Dougherty
*Assistant Examiner* — Nicholas E Kolderman

(57) ABSTRACT

A device for collecting a tissue sample includes an outer needle extending longitudinally from a proximal end to a distal end and including a lumen extending therethrough. The device also includes an inner needle extending longitudinally from a proximal end to a distal end and including an opening extending laterally in and along a length thereof. The inner needle is sized and shaped to be slidably received within the lumen of the outer needle and movable relative thereto between an insertion configuration, in which the opening is covered by the outer needle, to a tissue collecting configuration, in which the opening is exposed. In addition, the device includes a handle assembly for adjusting a throw length of the inner needle relative to the outer needle.

20 Claims, 2 Drawing Sheets

ADJUSTABLE THROW PERCUTANEOUS NEEDLE

CROSS-REFERENCE TO RELATED APPLICATIONS

This application claims the benefit of U.S. Provisional Application No. 62/121,099, filed Feb. 26, 2015 and entitled "ADJUSTABLE THROW PERCUTANEOUS NEEDLE," which is hereby incorporated by reference in its entirety.

BACKGROUND

Needle biopsy procedures are common for the diagnosis and the staging of disease. For example, a percutaneous biopsy needle may be introduced through an incision in the skin to a target tissue site. In certain clinical situations, however, it may be difficult to acquire a suitable sample. The more cells or tissue that can be acquired, the greater the potential for a definitive diagnosis.

SUMMARY

The present disclosure is directed to a device for collecting a tissue sample, comprising an outer needle extending longitudinally from a proximal end to a distal end and including a lumen extending therethrough along with an inner needle extending longitudinally from a proximal end to a distal end and including an opening extending laterally in and along a length thereof, the inner needle sized and shaped to be slidably received within the lumen of the outer needle and movable relative thereto between an insertion configuration, in which the opening is covered by the outer needle, to a tissue collecting configuration, in which the opening is exposed, and a handle assembly. The handle assembly includes a first handle member including a housing with a handle lumen extending longitudinally therethrough, the housing including an engaging element movable between an engaging configuration, in which the engaging element extends into the handle lumen, and a non-engaging configuration, in which the engaging element extends out of the handle lumen along with a second handle member including a shaft slidably received within the lumen and coupled to the proximal end of the inner needle, and a core member slidably coupled to a distal portion of the shaft and to a proximal end of the outer needle so that moving the second handle member longitudinally relative to the core member moves the inner and outer needles between the insertion configuration and the tissue collecting configuration, the core member including ratchet teeth along a length thereof for engaging the engaging element in the engaging configuration at a user-selected position to set a desired throw length by which the inner needle is to extend distally out of the outer needle in the tissue collecting configuration.

In an embodiment, the engaging element may be a pivoting pin pivoting between the engaging configuration, in which an engaging end of the pin extends into the handle lumen, and a non-engaging configuration, in which the engaging end of the pin is pivoted out of the handle lumen.

In an embodiment, the pin may be biased toward the engaging configuration via a spring element.

In an embodiment, the device may further comprise a spring member housed between the second handle member and the core member to bias the biopsy device toward the insertion configuration in which a distal end of the outer needle is distal of the inner needle.

In an embodiment, the ratchet teeth may extend along a length of the core member corresponding to up to a 2 cm throw length.

In an embodiment, the shaft of the second handle member may include a shoulder extending radially outward therefrom, the shoulder sized to contact the engaging element to contact the engaging element and move the engaging element toward the non-engaging configuration.

In an embodiment, the core member and the second handle member may be longitudinally slidable relative to one another via a pair of longitudinal grooves extending along opposing sides of the core member and pair of arms at a distal end of the shaft extending laterally inward to slidably engage the longitudinal grooves.

In an embodiment, the outer needle may include a distal cutting edge for cutting a tissue sample received within the opening from a surrounding tissue when the outer needle is moved distally over the inner needle.

The present disclosure is also directed to a handle assembly for adjusting a throw length of an inner needle of a biopsy device relative to an outer needle of the biopsy device, comprising a first handle member including a housing with a handle lumen extending longitudinally therethrough, the housing including an engaging element movable between an engaging configuration, in which the engaging element extends into the handle lumen, and a non-engaging configuration, in which the engaging element extends out of the handle lumen along with a second handle member including a shaft slidably received within the lumen and being coupled to a proximal end of the inner needle, and core member slidably coupled to a distal portion of the shaft and to a proximal end of the outer needle so that the inner needle passes through a lumen of the outer needle and moving the second handle member longitudinally relative to the core member moves the inner and outer needles between an insertion configuration and a tissue collecting configuration, the core member including ratchet teeth along a length thereof for engaging the engaging element in the engaging configuration to set a desired throw length by which the inner needle is to extend distally out of the outer needle in the tissue collecting configuration.

In an embodiment, the engaging element may be a pivoting pin pivoting between the engaging configuration, in which an engaging end of the pin extends into the handle lumen, and a non-engaging configuration, in which the engaging end of the pin is pivoted out of the handle lumen.

In an embodiment, the pin may be biased toward the engaging configuration via a spring element.

In an embodiment, the handle assembly may further comprise a spring member housed between the second handle member and the core member to bias the biopsy device toward the insertion configuration in which a distal end of the outer needle is distal of the inner needle.

In an embodiment, the ratchet teeth may extend along a length of the core member corresponding to up to a 2 cm throw length.

In an embodiment, the shaft of the second handle member may include a shoulder extending radially outward therefrom, the shoulder sized to contact the engaging element to contact the engaging element and move the engaging element toward the non-engaging configuration.

In an embodiment, the core member and the second handle member may be longitudinally slidable relative to one another via a pair of longitudinal grooves extending along opposing sides of the core member and pair of arms at a distal end of the shaft extending laterally inward to slidably engage the longitudinal grooves.

The present disclosure is also directed to a method for collecting a tissue sample, comprising inserting a distal portion of a biopsy device to a target tissue within a patient's body, the distal portion of the biopsy device including an outer needle and an inner needle slidably received therein, the inner needle including an opening extending laterally in and along a length thereof along with setting a desired throw length by which the inner needle is to extend distally out of the outer needle in a tissue collecting configuration by drawing a core member of a handle assembly proximally through a housing of a first handle member until ratchet teeth along the core member engage a portion of the housing at a user selected position, the handle assembly further including a second handle member connected to a proximal end of the inner needle and the core member connected to a proximal end of the outer needle, the core member and the second handle member slidably coupled to one another, and moving the second handle distally relative to the core member to move the device from an insertion configuration, in which the opening is covered by the outer needle, to a tissue collecting configuration, in which the inner needle extends distally from the outer needle by the desired throw length exposing the opening to receive a tissue sample therein.

BRIEF DESCRIPTION

DETAILED DESCRIPTION

Figure 1:
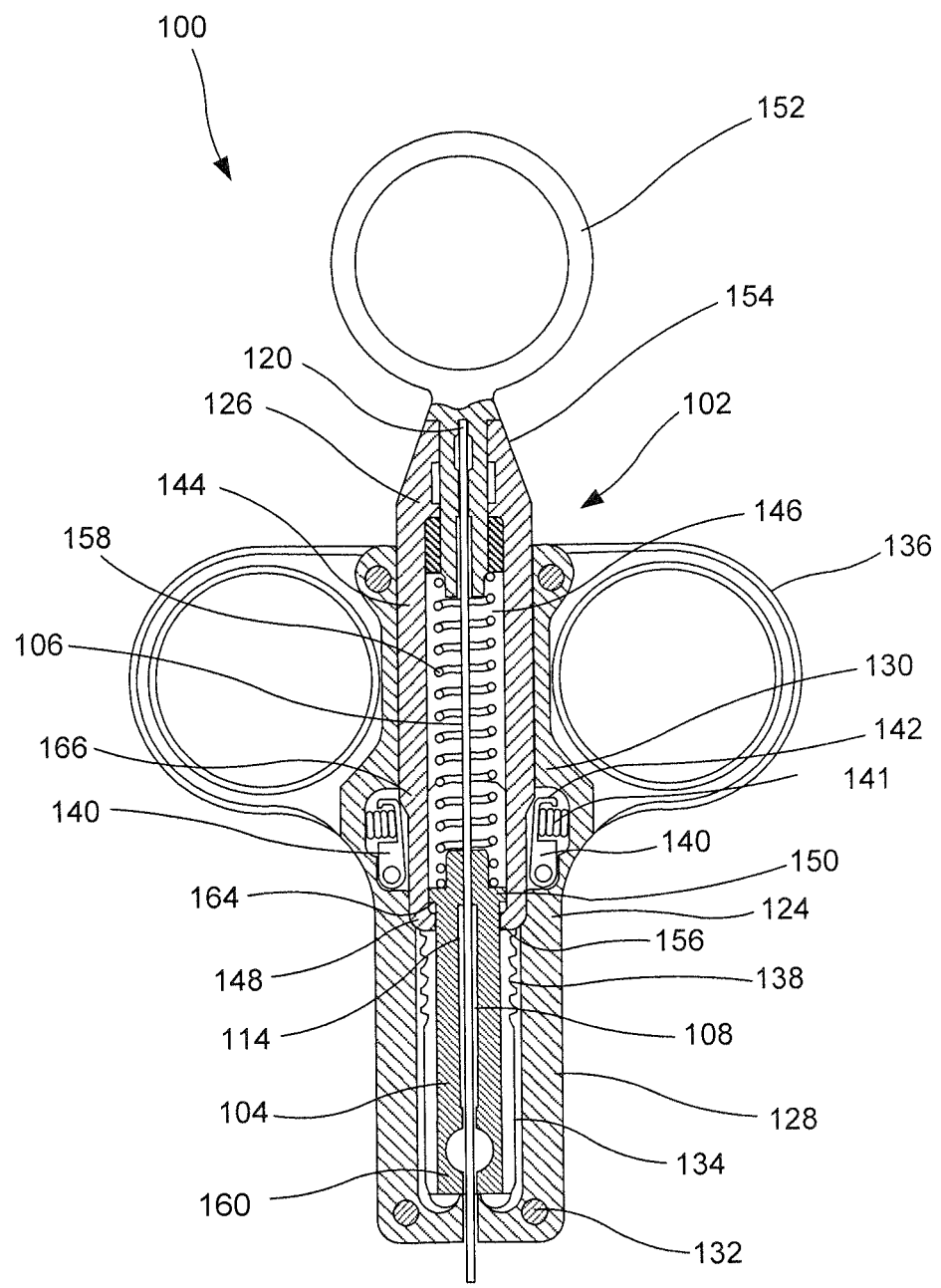
FIG. 1 shows a longitudinal cross-sectional view of a proximal portion of a device according to an exemplary embodiment of the present disclosure.

The present disclosure may be further understood with reference to the following description and the appended drawings, wherein like elements are referred to with the same reference numerals. The present disclosure is directed to a biopsy device and, in particular, to a percutaneous biopsy device. Exemplary embodiments of the present disclosure describe a biopsy device comprising a handle assembly which includes a ratchet mechanism configured to both cock a firing spring to fire an outer needle over an inner needle upon insertion of the inner needle in a target tissue, and set a desired throw length (i.e., a length of the inner and outer needles that is inserted into the target tissue). It should be noted that the terms "proximal" and "distal" refer to a direction toward (proximal) and away from (distal) a user of the device.

Figure 2:
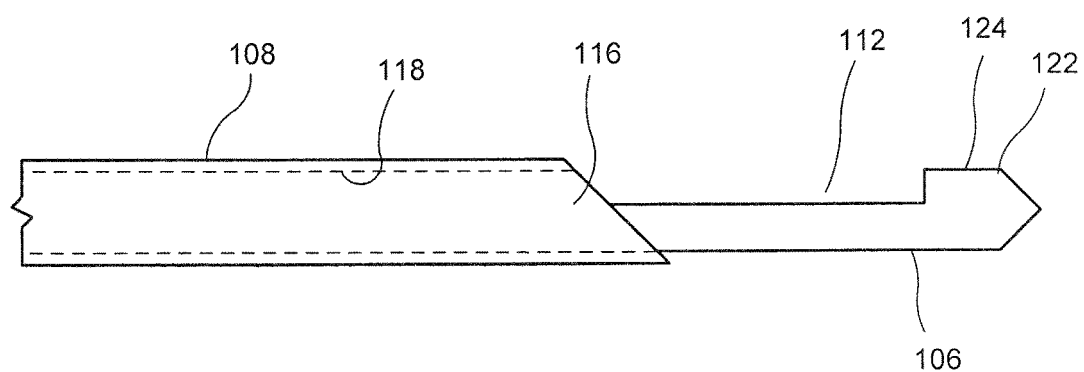
FIG. 2 shows a longitudinal cross-sectional device of a distal portion of the device of FIG. 1.
Figure 3:
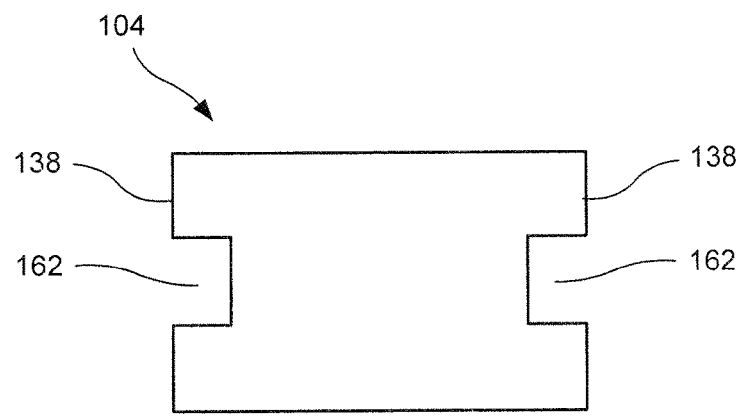
FIG. 3 shows a lateral cross-sectional view of a core member of the device of FIG. 1.

As shown in FIGS. 1-3, a biopsy device 100 according to an exemplary embodiment of the present disclosure comprises a handle assembly 102 including a ratcheted core member 104 for adjusting a desired throw length of an inner needle 106 relative to an outer needle 108 (e.g., a length of the inner needle 106 extending from a distal end 116 of the outer needle 108) and firing the outer needle 108 over the inner needle 106 to cut a tissue sample received within a notch or opening 112 of the inner needle 106 from surrounding tissue and trapping the tissue sample therein. The handle assembly 102 facilitates movement of the inner and outer needles 106, 108 from an insertion/withdrawal configuration, in which the opening 112 extending laterally into and along the inner needle 106 is completely covered by the outer needle 108, and a tissue collection configuration, in which a desired length of the opening 112 is exposed to collect a tissue therein.

The outer needle 108 extends longitudinally from a proximal end 114 to a distal end 116 and includes a lumen 118 extending longitudinally therethrough from the proximal end 114 to the distal end 116. The distal end 116 includes a sharpened tapered tip to facilitate piercing target tissue and a cutting edge to facilitate cutting of a tissue sample away from surrounding tissue as the outer needle 108 is moved over the inner needle 106 from the tissue collection configuration to the insertion/withdrawal configuration. The inner needle 106 is sized and shaped to be slidably received within the lumen 118 of the outer needle 108. The inner needle 106 extends longitudinally from a proximal end 120 to a distal end 122. The opening 112 extends laterally in and along a portion of a length of the inner needle 106 to allow for tissue collection therein. The opening 112 may be, for example, a notch or groove formed in the inner needle 106 to define a space in which tissue may be collected. Thus, when the device 100 is in the tissue collection configuration, any tissue received through the opening 112 is collected and trapped therein, when the needle 108 is passed over it.

In the insertion/withdrawal configuration, the inner needle 106 may be housed substantially within the outer needle 108 so that the distal end 122 of the inner needle 106 does not extend distally past the distal end 116 of the outer needle 108. In this configuration, the outer needle 108 extends over the inner needle 106 so that the opening 112 is covered by the outer needle 108 to prevent any tissue from being collected therethrough during insertion of the device 100 into the patient's body. In the tissue collecting configuration, the inner needle 106 is moved distally relative to the outer needle 108 such that the distal end 122 of the inner needle 106 extends distally past the distal end 116 of the outer needle 108, exposing a desired length of the opening 112 such that tissue may be collected therein. In other words, a desired length of the inner needle 106 is exposed distally of the distal end 116 of the outer needle 108. As will be described in further detail below, movement of the device 100 from the insertion/withdrawal configuration to the tissue collection configuration triggers a spring mechanism of the handle assembly 102 so that, upon collection of the tissue sample within the opening 112, the outer needle 108 is fired over the inner needle 106 to the insertion/withdrawal configuration, cutting and trapping the collected tissue sample within the opening 112 so that the device 100, including the tissue sample, may be withdrawn from the body.

The handle assembly 102 includes a first handle member 124 and a second handle member 126 slidably received within a portion of the first handle member 124 such that the first and second handle members 124, 126 are longitudinally movable relative to one another to move the inner and outer needles 106, 108 between the insertion/withdrawal configuration and the tissue collecting configuration. The handle assembly 102 also includes the core member 104 slidably coupled to a distal portion of the second handle member 126 and received within the first handle member 124. The second handle member 126 is connected to the proximal end 120 of the inner needle 106 while the core member 104 is connected to the proximal end 114 of the outer needle 108 so that the inner needle 106 passes through the lumen 118 of the outer needle 108. The core member 104 includes ratchet teeth 138 along a portion of a length thereof for engaging a pair of pivoting pins 140 within the first handle member 124 to adjust a throw length of the inner needle 106 relative to the outer needle 108.

The first handle member 124 includes an elongated housing 128 extending longitudinally from a proximal end 130 to a distal end 132 and including a handle lumen 134 extending therethrough. As would be understood by those skilled in the art, the first handle member 124 may also include fingerloops 136 or other ergonomic structures at the proximal end 130 of the housing 128. In an exemplary embodiment, the first handle member 124 may include two fingerloops 136, configured to receive an index finger and a middle finger, respectively. A pair of pivoting pins 140 are mounted within the housing 128 and biased toward an engaging configuration in which engaging ends 142 of the pins 140 project into the handle lumen 134 to engage the ratchet teeth 138 of the core member 104. The pins 140 according to this embodiment are biased toward the engaging configuration via, for example, a pair of springs 141. In a non-engaging configuration, the engaging ends 142 are pivoted out of the handle lumen 134 so that a portion of the second handle member 126 may be slidably received therebetween.

The second handle member 126 includes an elongated shaft 144 with a longitudinal recess 146 extending proximally therein from an open distal end 148. The elongated shaft 144 is sized and shaped to be received within the handle lumen 134 of the first handle member 124 while the longitudinal recess 146 is sized and shaped to slidably receive a proximal end 150 of the core member 104. The second handle member 126 according to this embodiment also includes a fingerloop 152 at a proximal end 154 of the elongated shaft 144. The fingerloop 152 may be particularly sized and shaped to receive a thumb of the user so that the second handle member 126 may be moved longitudinally relative to the first handle member 124 by simply moving the thumb toward and away from the index and middle fingers within the fingerloops 136 of the first handle member 124. The distal end 148 includes a pair of arms 156 extending laterally inward to engage a portion of the core member 104 received therebetween. In this embodiment, a spring 158 is housed within the longitudinal recess 146 to bias the proximal end 154 of the elongated shaft 144 away from the proximal end 150 of the core member 104.

The core member 104 extends longitudinally from a proximal end 150 to a distal end 160. The core member 104 includes a pair of longitudinal grooves 162, each of the longitudinal grooves 162 being sized and shaped to slidably receive a corresponding one of the arms 156. The longitudinal grooves 162, however, do not extend to the proximal end 150 of the core member 104 so that a proximal end 164 of the groove 162 acts as a stop prohibiting further distal movement of the core member 104 relative to the second handle member 126 and preventing the core member 104 from being disengaged therefrom. The ratchet teeth 138 extend along a portion of a length of the core member 104 corresponding to a potential throw length of the inner needle 106 relative to the outer needle 108. As shown in the lateral cross-section of the core member 104 illustrated in FIG. 3, the ratchet teeth 138 extend along opposing sides of the longitudinal grooves 162. In the insertion/withdrawal configuration, the core member 104 is in a distal-most position relative to the second handle member 126—i.e., the arms 156 at the distal end 148 of the shaft 144 abut the proximal end 164 of the longitudinal grooves 162. The core member 104 is biased toward this distal-most position via the spring 158. To move the device 100 toward the tissue collecting configuration, the second handle member 126 is moved distally relative to the core member 104, the arms 156 sliding distally along the longitudinal grooves 162.

To "cock" the device 100 (e.g., facilitate rapid firing of the outer needle 108 over the inner needle 106) and simultaneously adjust the throw length of the inner needle 106 relative to the outer needle 108, the second handle member 126 is drawn proximally relative to the first handle member 124, with the core member 104 in the distal-most position relative to the second handle member 126, until the ratchet teeth 138 of the core member 104 engage the pair of pins 140 and a desired throw length is achieved. In an exemplary embodiment, the ratchet teeth 138 along a portion of a length of the core member 104 with the length selected to, for example, permit up to a 2 cm throw in, for example, 2 mm increments. For example, pulling the second handle member 126 and the core member 104 assembly all the way back relative to the first handle member 124 allows for a 2 cm throw while pulling the second handle member 126 and the core member 104 halfway allows for a 1 cm throw. As would be understood by those skilled in the art, a different maximum throw length and different increments for the selectable throw lengths may be employed without departing from the scope of the disclosure. The ratchet teeth 138 are configured to permit the core member 104 to be moved proximally relative to the first handle member 124 against the pivoting pins 140, while preventing the core member 104 from being moved distally thereagainst.

Once the throw length has been adjusted, the second handle member 126 may be moved distally relative to the first handle member 124 and the core member 104—which is engaged via the pins 140 and thus prevented from moving distally relative thereto—toward the tissue collecting configuration so that the inner needle 106 extends distally out of the outer needle 108 by the desired throw length to collect the tissue sample through the exposed opening 112. The distal movement of the second handle member 126 relative to the first handle member 124 and the core member 104 compresses the spring 158 until a shoulder 166 along a length of the shaft 144 engages the pivoting pins 140, pivoting the pins 140 from the engaging configuration to the non-engaging configuration, out of engagement with the ratchet teeth 138. Upon disengagement of the pivoting pins 140 from the ratchet teeth 138, the spring 158 reverts toward its biased configuration, pushing the core member 104 distally relative second handle member 126 so that the outer needle 108 is rapidly "fired" over the inner needle 106, cutting the tissue sample received within the opening 112 from surrounding tissue and trapping the tissue sample in the needle 106.

According to an exemplary method for collecting a tissue sample using the device 100, a distal portion of the device 100 is inserted into a patient's body in the insertion/withdrawal configuration. In particular, the inner and outer needles 106, 108 are inserted to a target site within the patient's body via an incision in the skin or other opening while the handle assembly 102 remains outside of the body. Once inserted to the target site, the device 100 may be cocked by drawing the second handle member 126 proximally relative to the first handle member 124 until the ratchet teeth 138 of the core member 104 engage the pivoting pins 140 and a desired throw length is set. The second handle member 126 is then moved distally relative to the first handle member 124 to move the handle assembly 102 from the insertion/withdrawal configuration to the tissue collecting configuration, in which the opening 112 of the inner needle 106 is exposed distally of the distal end 116 of the outer needle 108 so that a tissue sample may be collected therein. As the inner needle 106 extends from outer needle 108 by the desired throw length, the shoulder 166 along the shaft 144 of the second handle member 126 causes the pivoting pins 140 to be disengage the ratchet teeth 138. Disengagement of the ratchet teeth 138 permits the core member 104 to revert to the biased, distal-most position relative to the second handle member 126, firing the outer needle 108 over the inner needle 106 to cut and trap the tissue sample within the opening 112.

It will be apparent to those skilled in the art that variations can be made in the structure and methodology of the present disclosure, without departing from the scope of the disclosure. Thus, it is intended that the present disclosure cover the modifications and variations of this disclosure provided that they come within the scope of the appended claims and their equivalents.

What is claimed is:

1. A device for collecting a tissue sample, comprising:
   an outer needle extending longitudinally from a proximal end to a distal end and including a lumen extending therethrough;
   an inner needle extending longitudinally from a proximal end to a distal end and including an opening extending laterally in and along a length thereof, the inner needle sized and shaped to be slidably received within the lumen of the outer needle and movable relative thereto between an insertion configuration, in which the opening is covered by the outer needle, to a tissue collecting configuration, in which the opening is exposed; and
   a handle assembly including:
      a first handle member including a housing with a handle lumen extending longitudinally therethrough, the housing including an engaging element movable between an engaging configuration, in which the engaging element extends into the handle lumen, and a non-engaging configuration, in which the engaging element extends out of the handle lumen;
      a second handle member including a shaft slidably received within the handle lumen and coupled to the proximal end of the inner needle;
      a spring member disposed within the second handle member; and
      a core member slidably coupled to a distal portion of the shaft and to a proximal end of the outer needle so that moving the second handle member longitudinally relative to the core member moves the inner and outer needles between the insertion configuration and the tissue collecting configuration, the core member including ratchet teeth along a length thereof for engaging the engaging element in the engaging configuration at a user-selected position to set a desired throw length by which the inner needle is to extend distally out of the outer needle in the tissue collecting configuration;
   wherein moving the second handle member towards the engaging element compresses the spring member against the core member.

2. The device of claim 1, wherein the engaging element is a pivoting pin pivoting between the engaging configuration, in which an engaging end of the pin extends into the handle lumen, and a non-engaging configuration, in which the engaging end of the pin is pivoted out of the handle lumen.

3. The device of claim 2, wherein the pin is biased toward the engaging configuration via a spring element.

4. The device of claim 1, wherein the further comprising a spring member is housed between the second handle member and the core member to bias the biopsy device toward the insertion configuration in which a distal end of the outer needle is distal of the inner needle.

5. The device of claim 1, wherein the ratchet teeth extend along a length of the core member corresponding to up to a 2 cm throw length.

6. The device of claim 1, wherein the shaft of the second handle member includes a shoulder extending radially outward therefrom, the shoulder sized to contact the engaging element and move the engaging element toward the non-engaging configuration.

7. The device of claim 1, wherein the core member and the second handle member are longitudinally slidable relative to one another via a pair of longitudinal grooves extending along opposing sides of the core member and pair of arms at a distal end of the shaft extending laterally inward to slidably engage the longitudinal grooves.

8. The device of claim 1, wherein the outer needle includes a distal cutting edge for cutting a tissue sample received within the opening from a surrounding tissue when the outer needle is moved distally over the inner needle.

9. A handle assembly for adjusting a throw length of an inner needle of a biopsy device relative to an outer needle of the biopsy device, comprising:
   a first handle member including a housing with a handle lumen extending longitudinally therethrough, the housing including an engaging element movable between an engaging configuration, in which the engaging element extends into the handle lumen, and a non-engaging configuration, in which the engaging element extends out of the handle lumen;
   a second handle member including a shaft slidably received within the handle lumen and being coupled to a proximal end of the inner needle;
   a spring member disposed within the second handle member; and
   a core member slidably coupled to a distal portion of the shaft and to a proximal end of the outer needle so that the inner needle passes through a lumen of the outer needle and moving the second handle member longitudinally relative to the core member moves the inner and outer needles between an insertion configuration and a tissue collecting configuration, the core member including ratchet teeth along a length thereof for engaging the engaging element in the engaging configuration to set a desired throw length by which the inner needle is to extend distally out of the outer needle in the tissue collecting configuration;
   wherein moving the second handle member towards the engaging element compresses the spring member against the core member.

10. The handle assembly of claim 9, wherein the engaging element is a pivoting pin pivoting between the engaging configuration, in which an engaging end of the pin extends into the handle lumen, and a non-engaging configuration, in which the engaging end of the pin is pivoted out of the handle lumen.

11. The handle assembly of claim 10, wherein the pin is biased toward the engaging configuration via a spring element.

12. The handle assembly of claim 9, wherein the spring member is housed between the second handle member and the core member to bias the biopsy device toward the insertion configuration in which a distal end of the outer needle is distal of the inner needle.

13. The handle assembly of claim 9, wherein the ratchet teeth extend along a length of the core member corresponding to up to a 2 cm throw length.

14. The handle assembly of claim 9, wherein the shaft of the second handle member includes a shoulder extending radially outward therefrom, the shoulder sized to contact the engaging element and move the engaging element toward the non-engaging configuration.

15. The handle assembly of claim 9, wherein the core member and the second handle member are longitudinally slidable relative to one another via a pair of longitudinal grooves extending along opposing sides of the core member and pair of arms at a distal end of the shaft extending laterally inward to slidably engage the longitudinal grooves.

16. A method for collecting a tissue sample, comprising:
inserting a distal portion of a biopsy device to a target tissue within a patient's body, the distal portion of the biopsy device including an outer needle and an inner needle slidably received therein, the inner needle including an opening extending laterally in and along a length thereof;
setting a desired throw length by which the inner needle is to extend distally out of the outer needle in a tissue collecting configuration by drawing a core member of a handle assembly proximally through a housing of a first handle member until ratchet teeth along the core member engage a portion of the housing at a user selected position, the handle assembly further including a second handle member connected to a proximal end of the inner needle and the core member connected to a proximal end of the outer needle, the core member and the second handle member slidably coupled to one another; and
moving the second handle member distally such that the second handle member compresses a spring member against the core member to move the device from an insertion configuration, in which the opening is covered by the outer needle, to a tissue collecting configuration, in which the inner needle extends distally from the outer needle by the desired throw length exposing the opening to receive a tissue sample therein.

17. The method of claim 16, wherein, upon collecting the tissue sample in the opening, the device reverts to the insertion configuration, the handle assembly including the spring between the second handle member and the core member biasing the device toward the insertion configuration.

18. The method of claim 17, wherein setting the desired throw length includes engaging the ratchet teeth with an engaging pin of the housing which, when in an engaging configuration extends into a handle lumen extending through the housing.

19. The method of claim 18, wherein, when the second handle member is moved distally relative to the core member, a shoulder extending radially outward therefrom contacts the engaging pin to move the engaging in to a non-engaging configuration in which the engaging pin is pivoted out of the handle lumen to release the core member, permitting the device to revert to its biased insertion configuration.

20. The method of claim 16, wherein, as the device reverts to the biased insertion configuration, a distal cutting edge of the outer needle cuts the tissue sample from a surrounding tissue and traps the tissue sample within the opening.

* * * * *